United States Patent
Rehbein et al.

(10) Patent No.: US 12,156,787 B2
(45) Date of Patent: Dec. 3, 2024

(54) AREA MANAGEMENT OF TISSUE SITES ON ARTICULATING JOINTS

(71) Applicant: Solventum Intellectual Properties Company, Maplewood, MN (US)

(72) Inventors: Jonathan G. Rehbein, San Antonio, TX (US); Luke Perkins, San Antonio, TX (US); David Richard Mercer, San Antonio, TX (US); Richard Marvin Kazala, Jr., San Antonio, TX (US); Larry Tab Randolph, San Antonio, TX (US)

(73) Assignee: Solventum Intellectual Properties Company, Maplewood, MN (US)

( * ) Notice: Subject to any disclaimer, the term of this patent is extended or adjusted under 35 U.S.C. 154(b) by 92 days.

(21) Appl. No.: 16/757,642

(22) PCT Filed: Oct. 23, 2018

(86) PCT No.: PCT/US2018/057073
§ 371 (c)(1),
(2) Date: Apr. 20, 2020

(87) PCT Pub. No.: WO2019/083979
PCT Pub. Date: May 2, 2019

(65) Prior Publication Data
US 2020/0330285 A1    Oct. 22, 2020

Related U.S. Application Data

(60) Provisional application No. 62/575,961, filed on Oct. 23, 2017.

(51) Int. Cl.
*A61F 13/05* (2024.01)
*A61B 46/20* (2016.01)
(Continued)

(52) U.S. Cl.
CPC .............. *A61F 13/05* (2024.01); *A61B 46/20* (2016.02); *A61F 13/06* (2013.01); *A61L 15/425* (2013.01);
(Continued)

(58) Field of Classification Search
CPC ............ A61F 13/00068; A61F 13/0216; A61F 13/06; A61F 2013/00174; A61F 13/0006;
(Continued)

(56) References Cited

U.S. PATENT DOCUMENTS

| | | |
|---|---|---|
| 1,355,846 A | 10/1920 | Rannells |
| 2,547,758 A | 4/1951 | Keeling |

(Continued)

FOREIGN PATENT DOCUMENTS

| | | |
|---|---|---|
| AU | 550575 B2 | 3/1986 |
| AU | 745271 B2 | 3/2002 |

(Continued)

OTHER PUBLICATIONS

International Search Report and Written Opinion for Corresponding Application No. PCT/US2018/057073, mailed Jan. 17, 2019.
(Continued)

*Primary Examiner* — Susan S Su
*Assistant Examiner* — Eric Rassavong

(57) ABSTRACT

A dressing for managing an incision and surrounding tissue where edema and swelling may be present post-operation. The dressing may maximize coverage of area in articulating joints, such as a knee or elbow, while allowing for substantial range of motion. In some embodiments, the dressing may comprise an adhesive border configured to be adhered to skin around an articulating joint, a skin-interfacing fabric for minimizing skin irritation, a foam body for manifolding negative pressure and absorbing exudate and other body fluids, and a thin polymer film cap for sealing the assembly (Continued)

so negative pressure can be maintained throughout the dressing.

20 Claims, 10 Drawing Sheets

(51) Int. Cl.
    *A61F 13/00*           (2024.01)
    *A61F 13/06*           (2006.01)
    *A61L 15/42*           (2006.01)
    *A61M 1/00*          (2006.01)

(52) U.S. Cl.
    CPC .............. *A61M 1/75* (2021.05); *A61M 1/915* (2021.05); *A61M 1/96* (2021.05); *A61B 2046/205* (2016.02); *A61F 2013/00174* (2013.01); *A61M 1/917* (2021.05); *A61M 2210/086* (2013.01)

(58) Field of Classification Search
    CPC ... A61F 13/05; A61B 46/20; A61B 2046/205; A61L 15/425; A61M 1/75; A61M 1/90; A61M 1/85; A61M 2210/086; A61M 1/917
    See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| D348,106 S * | 6/1994 | Mason .......................... D24/207 |
| 5,342,376 A | 8/1994 | Ruff |
| 5,344,415 A * | 9/1994 | DeBusk .............. A61F 13/0206 604/304 |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,469,913 B1 | 6/2013 | Jon |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0093050 A1 | 5/2003 | Baker |

(56) References Cited

U.S. PATENT DOCUMENTS

| | | | |
|---|---|---|---|
| 2005/0147656 A1* | 7/2005 | McCarthy | A61F 13/01034 424/445 |
| 2008/0195012 A1 | 8/2008 | Miros et al. | |
| 2009/0270827 A1* | 10/2009 | Gundersen | A61F 13/0209 156/78 |
| 2009/0299342 A1* | 12/2009 | Cavanaugh, II | A61F 13/0223 604/543 |
| 2010/0210986 A1* | 8/2010 | Sanders | A61M 1/90 602/41 |
| 2012/0022436 A1* | 1/2012 | Bradley | A61M 35/30 604/23 |
| 2012/0209226 A1 | 8/2012 | Simmons et al. | |
| 2014/0012169 A1* | 1/2014 | Wilford | A61H 1/008 601/151 |
| 2014/0163491 A1 | 6/2014 | Schuessler et al. | |
| 2014/0276288 A1* | 9/2014 | Randolph | A61H 9/0057 601/152 |
| 2015/0080788 A1 | 3/2015 | Blott et al. | |
| 2015/0313762 A1 | 11/2015 | Simmons et al. | |
| 2015/0359951 A1 | 12/2015 | Andersen et al. | |
| 2016/0045374 A1 | 2/2016 | Vitaris | |
| 2016/0045375 A1 | 2/2016 | Zurovcik | |
| 2016/0120706 A1 | 5/2016 | Collinson et al. | |
| 2017/0189236 A1* | 7/2017 | Locke | A61M 1/80 |
| 2019/0117465 A1* | 4/2019 | Osborne | A61F 13/00029 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2012/057881 A1 | 5/2012 |
| WO | 2012112204 A1 | 8/2012 |
| WO | 2013114097 A1 | 8/2013 |
| WO | 2013/149078 A1 | 10/2013 |
| WO | WO-2018212849 A1 * | 11/2018 ....... A61F 13/00068 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al.; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al.; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Bjom et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic

(56) References Cited

OTHER PUBLICATIONS

Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
U.S. Non-Final Office Action Corresponding to U.S. Appl. No. 16/166,424, mailed Feb. 2, 2022.
Chinese First Office Action Corresponding to Application No. 2018800749844, mailed Jul. 5, 2021.
Office Action for related U.S. Appl. No. 16/166,424, dated Aug. 18, 2023.
1 European Office Action for related application 21183813.1, dated May 3, 2023.
Austarialian Examination Report for corresponding application 2018355151, dated Mar. 20, 2024.

\* cited by examiner

AREA MANAGEMENT OF TISSUE SITES ON ARTICULATING JOINTS

RELATED APPLICATION

This present invention claims the benefit, under 35 USC 119(e), of the filing of U.S. Provisional Patent Application Ser. No. 62/575,961, entitled "Area Management of Tissue Sites on Articulating Joints", filed Oct. 23, 2017, and is incorporated herein by reference in its entirety.

TECHNICAL FIELD

The invention set forth in the appended claims relates generally to tissue treatment systems and more particularly, but without limitation, to area management of incisions and other tissue sites on articulating joints.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes may benefit healthcare providers and patients.

BRIEF SUMMARY

New and useful systems, apparatuses, and methods for managing tissue sites in a negative-pressure therapy environment are set forth in the appended claims. Illustrative embodiments are also provided to enable a person skilled in the art to make and use the claimed subject matter.

For example, such an apparatus may be a dressing for managing an incision and surrounding tissue where edema and swelling may be present post-operation. The dressing may maximize coverage of area in articulating joints, such as a knee or elbow, while allowing for substantial range of motion. In some embodiments, the dressing may comprise an adhesive border configured to be adhered to skin around an articulating joint, a skin-interfacing fabric for minimizing skin irritation, a foam body for manifolding negative pressure and absorbing exudate and other body fluids, and a thin polymer film cap for sealing the assembly so negative pressure can be maintained throughout the dressing. In some embodiments, the dressing may have one or more portions which can be cut to customize the size of the dressing. Separate adhesive films can be applied over the cut portions for sealing.

More generally, a dressing for treating an area around an articulating joint may comprise an attachment device, such as a sealing ring, having a treatment aperture; a manifold comprising a stem, a first arm joined to the stem, and a second arm joined to the stem; a cover disposed over the manifold and coupled to the attachment device around the manifold; and an adhesive on the attachment device configured to bond to the area around the articulating joint. The manifold may be at least partially exposed through the treatment aperture.

In some embodiments, the manifold may comprise a first arm having a greater span than the second arm. The first arm and the second arm may flare away from the stem in some embodiments. The manifold may comprise a face that is biconcave in some embodiments. For example, the stem, the first arm, and the second arm may define a concave void on opposing sides of the manifold.

Other aspects of the dressing may comprise a manifold having a first portion configured to be disposed over an articulating surface of a limb; a second portion configured to be at least partially wrapped around a proximal portion of the limb; and a third portion configured to be at least partially wrapped around a distal portion of the limb. For example, the first portion may be positioned over a knee. The dressing may have an opening or void on each side of the first portion between the second portion and the third portion. In some aspects, the second portion and the third portion may have converging edges. In some aspects, the second portion and the third portion may flare away from a midline of the first portion.

An example method of treating an area around an articulating joint of a limb may comprise applying the dressing so that a stem of the dressing is disposed over the articulating joint; wrapping a first arm of the dressing around a proximal portion of the limb; wrapping a second arm around a distal portion of the limb; fluidly coupling a negative-pressure source to the manifold; and applying negative-pressure from the negative-pressure source.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
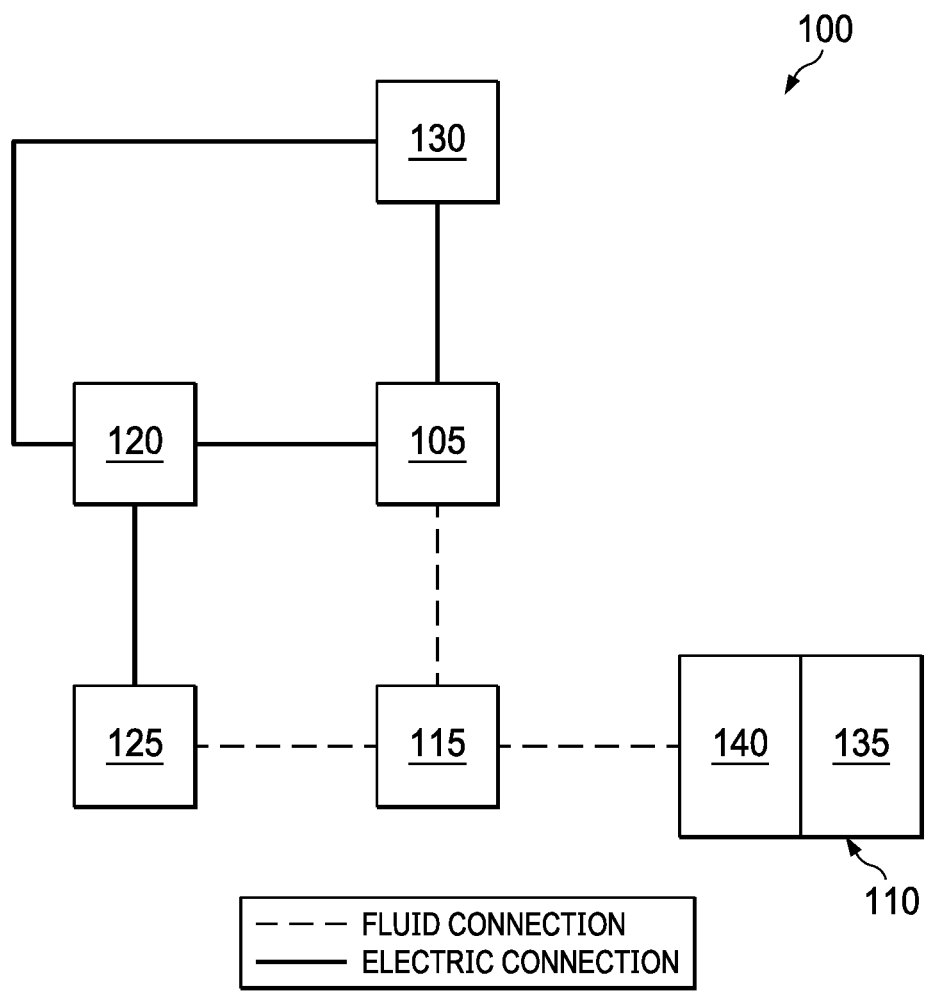
FIG. 1 is a functional block diagram of an example embodiment of a therapy system that can provide negative-pressure treatment in accordance with this specification.

FIG. 1 is a simplified functional block diagram of an example embodiment of a therapy system 100 that can provide negative-pressure therapy to a tissue site in accordance with this specification.

The term "tissue site" in this context broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 105, a dressing 110, a fluid container, such as a container 115, and a regulator or controller, such as a controller 120, for example. Additionally, the therapy system 100 may include sensors to measure operating parameters and provide feedback signals to the controller 120 indicative of the operating parameters. As illustrated in FIG. 1, for example, the therapy system 100 may include one or more sensors coupled to the controller 120, such as a first sensor 125 and a second sensor 130. As illustrated in the example of FIG. 1, the dressing 110 may comprise or consist essentially of a tissue interface 135, a cover 140, or both in some embodiments.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the controller 120 and other components into a therapy unit.

In general, components of the therapy system 100 may be coupled directly or indirectly. For example, the negative-pressure source 105 may be directly coupled to the container 115, and may be indirectly coupled to the dressing 110 through the container 115. Coupling may include fluid, mechanical, thermal, electrical, or chemical coupling (such as a chemical bond), or some combination of coupling in some contexts. For example, the negative-pressure source 105 may be electrically coupled to the controller 120, and may be fluidly coupled to one or more distribution components to provide a fluid path to a tissue site. In some embodiments, components may also be coupled by virtue of physical proximity, being integral to a single structure, or being formed from the same piece of material.

A distribution component is preferably detachable, and may be disposable, reusable, or recyclable. The dressing 110 and the container 115 are illustrative of distribution components. A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 110. For example, such a dressing interface may be a SENSA-T.R.A.C.™ Pad available from KCI of San Antonio, Tex.

A negative-pressure supply, such as the negative-pressure source 105, may be a reservoir of air at a negative pressure, or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 115 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 120, may be a microprocessor or computer programmed to operate one or more components of the therapy system 100, such as the negative-pressure source 105. In some embodiments, for example, the controller 120 may be a microcontroller, which generally comprises an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the tissue interface 135, for example. The controller 120 is also preferably configured to receive one or more input signals, such as a feedback signal, and programmed to modify one or more operating parameters based on the input signals.

Sensors, such as the first sensor 125 and the second sensor 130, are generally known in the art as any apparatus operable to detect or measure a physical phenomenon or property, and generally provide a signal indicative of the phenomenon or property that is detected or measured. For example, the first sensor 125 and the second sensor 130 may be configured to measure one or more operating parameters of the therapy system 100. In some embodiments, the first sensor 125 may be a transducer configured to measure pressure in a pneumatic pathway and convert the measurement to a signal indicative of the pressure measured. In some embodiments, for example, the first sensor 125 may be a piezoresistive strain gauge. The second sensor 130 may optionally measure operating parameters of the negative-pressure source 105, such as the voltage or current, in some embodiments. Preferably, the signals from the first sensor 125 and the second sensor 130 are suitable as an input signal to the controller 120, but some signal conditioning may be appropriate in some embodiments. For example, the signal may need to be filtered or amplified before it can be processed by the controller 120. Typically, the signal is an electrical signal, but may be represented in other forms, such as an optical signal.

The tissue interface 135 can be generally adapted to partially or fully contact a tissue site. The tissue interface 135 may take many forms, and may have many sizes, shapes, or thicknesses depending on a variety of factors, such as the type of treatment being implemented or the nature and size of a tissue site. For example, the size and shape of the tissue interface 135 may be adapted to the contours of deep and irregular shaped tissue sites. Moreover, any or all of the surfaces of the tissue interface 135 may have projections or an uneven, course, or jagged profile that can induce strains and stresses on a tissue site, which can promote granulation at the tissue site.

In some embodiments, the tissue interface 135 may be a manifold. A "manifold" in this context generally includes any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be interconnected to improve distribution or collection of fluids across a tissue site. In some illustrative embodiments, a manifold may be a porous foam material having interconnected cells or pores. For example, open-cell foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

The average pore size of foam may vary according to needs of a prescribed therapy. For example, in some embodiments, the tissue interface 135 may be foam having pore sizes in a range of 400-600 microns. The tensile strength of the tissue interface 135 may also vary according to needs of a prescribed therapy. For example, the tensile strength of foam may be increased for instillation of topical treatment solutions. In some examples, the tissue interface 135 may be reticulated polyurethane foam such as found in GRANUFOAM™ dressing or V.A.C. VERAFLO™ dressing, both available from KCI of San Antonio, Tex.

The tissue interface 135 may be either hydrophobic or hydrophilic. In an example in which the tissue interface 135 may be hydrophilic, the tissue interface 135 may also wick fluid away from a tissue site, while continuing to distribute negative pressure to the tissue site. The wicking properties of the tissue interface 135 may draw fluid away from a tissue site by capillary flow or other wicking mechanisms. An example of hydrophilic foam is a polyvinyl alcohol, open-cell foam such as V.A.C. WHITEFOAM™ dressing available from KCI of San Antonio, Tex. Other hydrophilic foams may include those made from polyether. Other foams that may exhibit hydrophilic characteristics include hydrophobic foams that have been treated or coated to provide hydrophilicity.

The tissue interface 135 may further promote granulation at a tissue site when pressure within the sealed therapeutic environment is reduced. For example, any or all of the surfaces of the tissue interface 135 may have an uneven, coarse, or jagged profile that can induce microstrain and stress at a tissue site if negative pressure is applied through the tissue interface 135.

In some embodiments, the tissue interface 135 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 135 may further serve as a scaffold for new cell-growth, or a scaffold material may be used in conjunction with the tissue interface 135 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 140 may provide a bacterial barrier and protection from physical trauma. The cover 140 may also be constructed from a material that can reduce evaporative losses and provide a fluid seal between two components or two environments, such as between a therapeutic environment and a local external environment. For example, the cover 140 may comprise or consist essentially of an elastomeric film or membrane that can provide a seal adequate to maintain a negative pressure at a tissue site for a given negative-pressure source. In some example embodiments, the cover 140 may be a polymer drape, such as a polyurethane film, that is permeable to water vapor but impermeable to liquid. The cover 140 may have a high moisture-vapor transmission rate (MVTR) in some applications. For example, the MVTR may be at least 250 g/m^2 per twenty-four hours in some embodiments (based on ASTM E96/E96M for upright cup measurement). Such drapes typically have a thickness in the range of 25-50 microns. For permeable materials, the permeability generally should be low enough that a desired negative pressure may be maintained.

An attachment device may be used to attach the cover 140 to an attachment surface, such as undamaged epidermis, a gasket, or another cover. The attachment device may take many forms. For example, an attachment device may be a medically-acceptable, pressure-sensitive adhesive configured to bond the cover 140 to epidermis around a tissue site. In some embodiments, for example, some or all of the cover 140 may be coated with an adhesive, such as an acrylic adhesive, which may have a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

Figure 2:
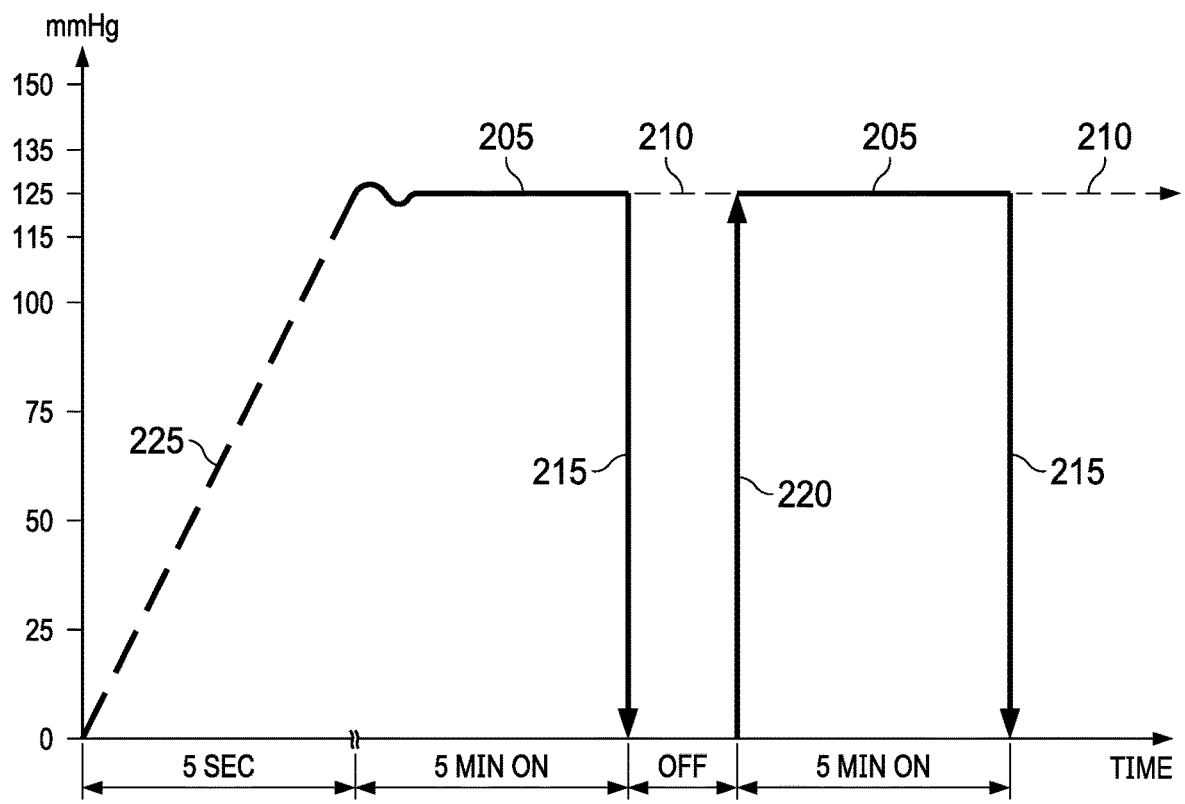
FIG. 2 is a graph illustrating additional details of example pressure control modes that may be associated with some embodiments of the therapy system of FIG. 1.

FIG. 2 is a graph illustrating additional details of an example control mode that may be associated with some embodiments of the controller 120. In some embodiments, the controller 120 may have a continuous pressure mode, in which the negative-pressure source 105 is operated to provide a constant target negative pressure, as indicated by line 205 and line 210, for the duration of treatment or until manually deactivated. Additionally or alternatively, the controller may have an intermittent pressure mode, as illustrated in the example of FIG. 2. In FIG. 2, the x-axis represents time, and the y-axis represents negative pressure generated by the negative-pressure source 105 over time. In the example of FIG. 2, the controller 120 can operate the negative-pressure source 105 to cycle between a target pressure and atmospheric pressure. For example, the target pressure may be set at a value of 125 mmHg, as indicated by line 205, for a specified period of time (e.g., 5 min), followed by a specified period of time (e.g., 2 min) of deactivation, as indicated by the gap between the solid line 215 and the solid line 220. The cycle can be repeated by activating the negative-pressure source 105, as indicated by the solid line 220, which can form a square wave pattern between the target pressure and atmospheric pressure.

In some example embodiments, the increase in negative-pressure from ambient pressure to the target pressure may not be instantaneous. For example, the negative-pressure source 105 and the dressing 110 may have an initial rise time, as indicated by the dashed line 225. The initial rise time may vary depending on the type of dressing and therapy equipment being used. For example, the initial rise time for one therapy system may be in a range of about 20-30 mmHg/second and in a range of about 5-10 mmHg/second for another therapy system. If the therapy system 100 is operating in an intermittent mode, the repeating rise time as indicated by the solid line 220 may be a value substantially equal to the initial rise time as indicated by the dashed line 225.

Figure 3:
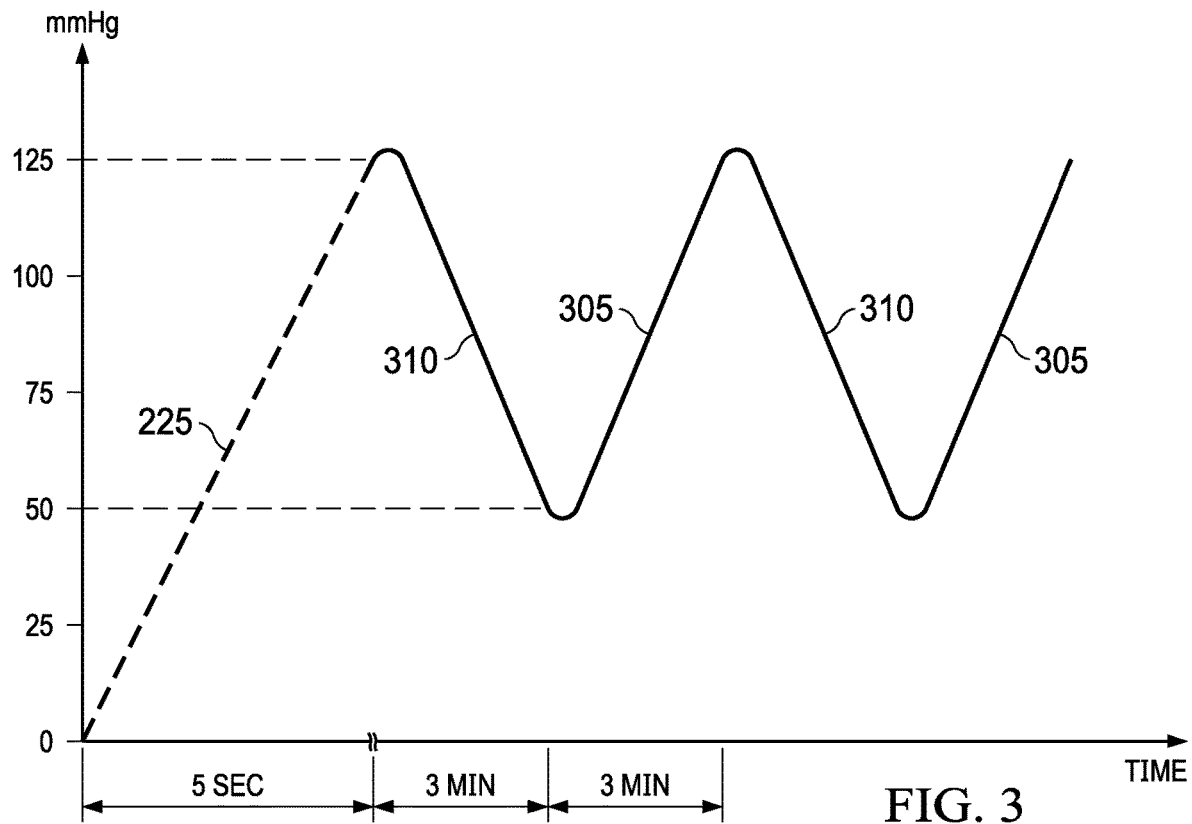
FIG. 3 is a graph illustrating additional details that may be associated with another example pressure control mode in some embodiments of the therapy system of FIG. 1.

FIG. 3 is a graph illustrating additional details that may be associated with another example pressure control mode in some embodiments of the therapy system 100. In FIG. 3, the x-axis represents time and the y-axis represents negative pressure generated by the negative-pressure source 105. The target pressure in the example of FIG. 3 can vary with time in a dynamic pressure mode. For example, the target pressure may vary in the form of a triangular waveform, varying between a minimum and maximum negative pressure of 50-125 mmHg with a rise time 305 set at a rate of +25 mmHg/min. and a descent time 310 set at -25 mmHg/min, respectively. In other embodiments of the therapy system 100, the triangular waveform may vary between negative pressure of 25-125 mmHg with a rise time 305 set at a rate of +30 mmHg/min and a descent time 310 set at -30 mmHg/min.

In some embodiments, the controller 120 may control or determine a variable target pressure in a dynamic pressure mode, and the variable target pressure may vary between a maximum and minimum pressure value that may be set as an input prescribed by an operator as the range of desired negative pressure. The variable target pressure may also be processed and controlled by the controller 120, which can vary the target pressure according to a predetermined waveform, such as a triangular waveform, a sine waveform, or a saw-tooth waveform. In some embodiments, the waveform may be set by an operator as the predetermined or time-varying negative pressure desired for therapy.

Figure 4:
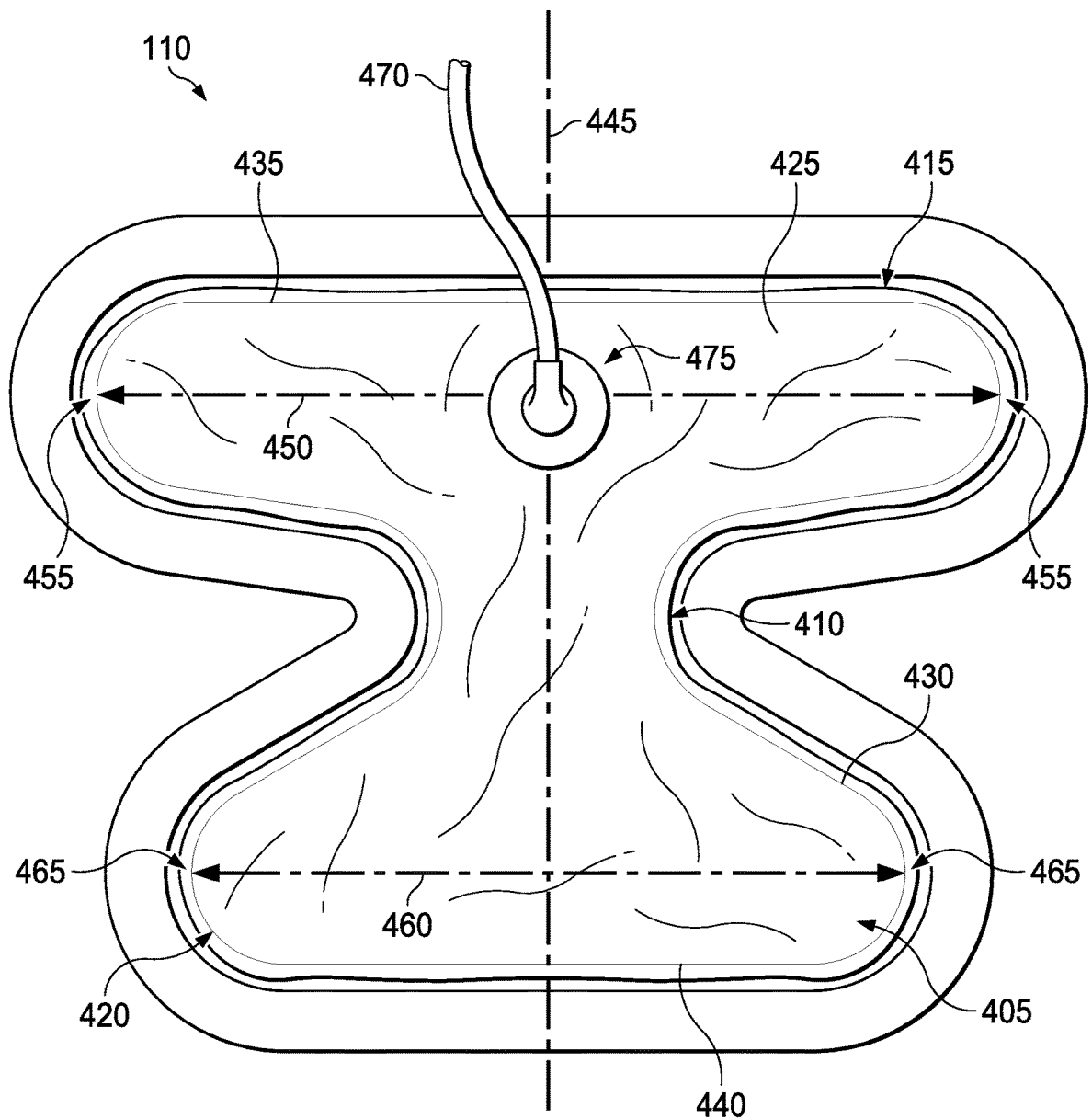
FIG. 4 is a top view of a dressing illustrating additional details that may be associated with an example embodiment of therapy system of FIG. 1.

FIG. 4 is a top view of an example of the dressing 110, illustrating additional details that may be associated with some embodiments. In the example embodiment of FIG. 4, the dressing 110 includes features that can cover articulating joints, such as a knee, while still allowing for significant range of motion. For example, the dressing 110 of FIG. 4 generally comprises a manifold 405 having a stem 410, a first arm 415 joined to a first end of the stem 410, and a second arm 420 joined to a second end of the stem 410.

In some embodiments, the manifold 405 may be characterized as a polyhedron or as a generalized cylinder. For example, in FIG. 4 the manifold 405 can be characterized as a generalized cylinder having a face 425 and an edge 430. The edge 430 in FIG. 4 bounds the stem 410, the first arm 415, and the second arm 420. In some embodiments, some portions of the edge 430 may be curved, and some portions may be straight. In FIG. 4, for example, the first arm 415 is bounded in part by a first edge portion 435 that is substantially straight, and the second arm 420 is bounded in part by a second edge portion 440 that is substantially straight. In other embodiments, the first arm 415, the second arm 420, or both may be contoured at the extremities.

The stem 410 is generally configured to be positioned over an articular surface. The width of the stem 410 may vary for different types of joints, and may be limited to minimize interference with articulation. For example, in some embodiments, the stem 410 may be configured for positioning over a patella and have a width of 2-4 inches. In other examples, a width of 1-3 inches may be suitable for positioning over an olecranon.

As illustrated in the example of FIG. 4, the first arm 415 and the second arm 420 may flare away from the stem 410. In some examples, the face 425 may be biconcave. More generally, portions of the edge 430 bounding the first arm 415 and the second arm 420 may be biconcave, converging toward the stem 410 to define a concave void adjacent to each side of the stem 410. In the example of FIG. 4, the concave void is curved. In other examples, the edge 430 may have straight segments that converge toward a vertex at the stem 410.

Some embodiments of the manifold 405 may additionally be characterized by a line of symmetry 445 through the stem 410, and each of the first arm 415 and the second arm 420 may be characterized by a span that is generally orthogonal to the line of symmetry 445. In the example of FIG. 4, a first span 450 between extremities 455 is characteristic of the first arm 415, and a second span 460 between extremities 465 is characteristic of the second arm 420.

In the example of FIG. 4, the first span 450 is greater than the second span 460. A suitable ratio of the span of the first span 450 to the second span 460 may generally be in a range of 1.2 to 3.4. A ratio of 1.2 to 1.6 may be particularly advantageous for some applications. For example, in some embodiments the first span 450 may be in a range of 30-65 centimeters and the second span 460 may be in a range of 20-45 centimeters. In other examples, the first span 450 may be in a range of 15-50 centimeters and the second span 460 may be in a range of 8-25 centimeters.

In some embodiments, a fluid conductor 470 may be coupled to the dressing 110. As illustrated in FIG. 4, the fluid conductor 470 may be coupled to the first arm 415. FIG. 4 also illustrates an example of a dressing interface 475 that may be used to facilitate fluidly coupling the fluid conductor 470 to the manifold 405.

Figure 5:
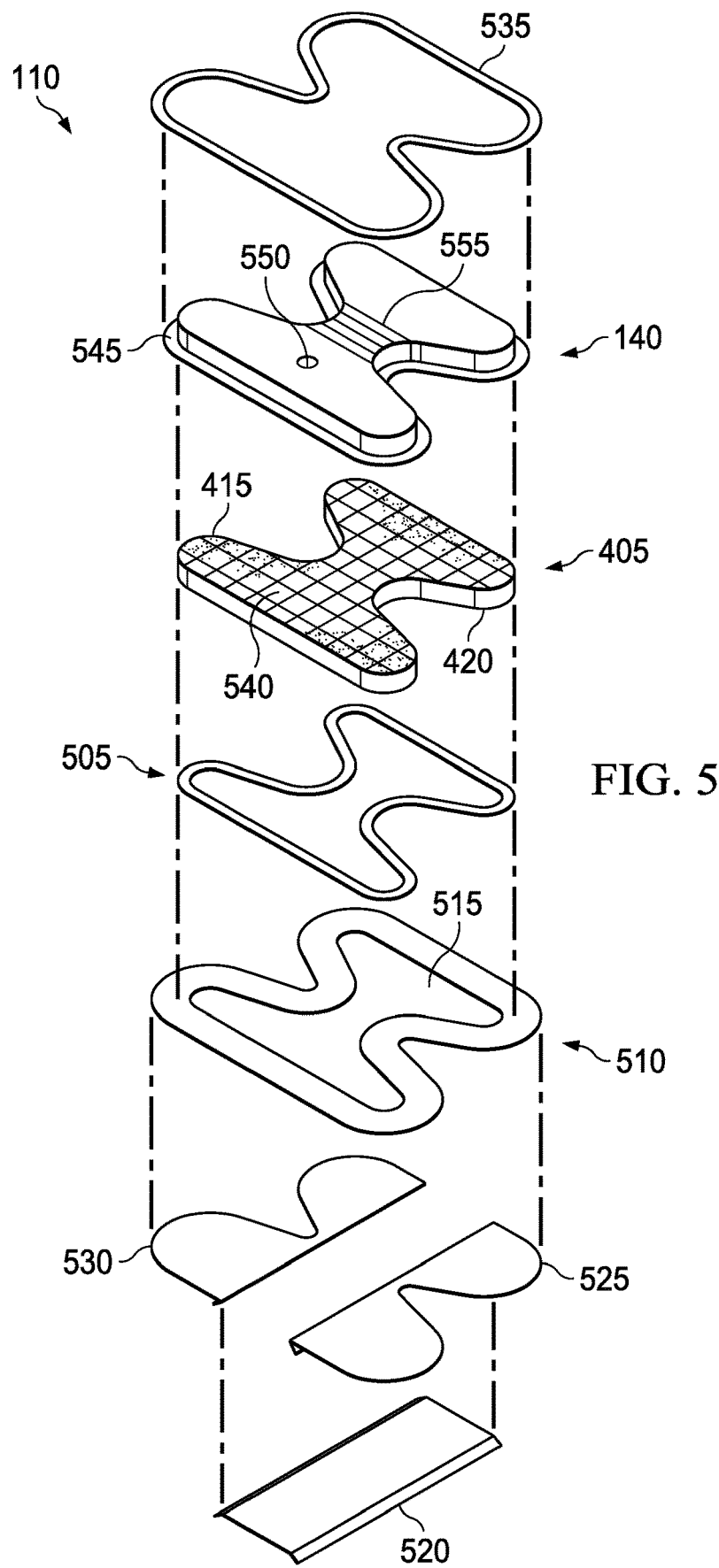
FIG. 5 is an assembly view of the dressing of FIG. 4, illustrating additional details that may be associated with some examples.

FIG. 5 is an assembly view of the dressing 110 of FIG. 4, illustrating additional details that may be associated with some examples. In the example of FIG. 5, the cover 140, the manifold 405, an adhesive ring 505, and an attachment device 510 with a treatment area aperture 515 are disposed in a stacked relationship. In general, the cover 140, the manifold 405, the adhesive ring 505, and the attachment device 510 of FIG. 5 have similar shapes. The attachment device 510 may be slightly larger than the manifold 405, and the adhesive ring 505 can bond a peripheral portion of the manifold 405 to an interior portion of the attachment device 510. The manifold 405 can be exposed through the treatment area aperture 515. In some embodiments, an adhesive may be disposed on at least portions of the manifold 405 exposed through the treatment area aperture 515. For example, portions of the first arm 415, the second arm 420, or both may have an adhesive coating. In some embodiments, the adhesive may be pattern-coated, and may cover up to 50% of the surface. The dressing 110 may optionally include one or more release liners, such as a center release liner 520, a first side release liner 525, and a second side release liner 530. In some examples, the dressing 110 may have two release liners, each of which may have perforations or slits configured to allow the release liners to be separated into smaller pieces for removal. Additionally, some embodiments may also have one or more casting sheet liners 535.

In some embodiments, the attachment device 510 may be a sealing ring. Similar or analogous to the cover 140, a suitable sealing ring may be, for example, an elastomeric film or membrane that can provide a seal in a therapeutic negative-pressure environment. In some example embodiments, the attachment device 510 may be a polymer film, such as a polyurethane film, that is permeable to water vapor but impermeable to liquid. The attachment device 510 typically has a thickness in the range of 25-50 microns. For permeable materials, the permeability generally should be low enough that a desired negative pressure may be maintained. The attachment device 510 may also include a medically-acceptable, pressure-sensitive adhesive. In some embodiments, for example, the attachment device 510 may be a polymer film coated with an adhesive, such as an acrylic adhesive, which may have a coating weight between 25-65 grams per square meter (g.s.m.). Thicker adhesives, or combinations of adhesives, may be applied in some embodiments to improve the seal and reduce leaks. Additionally or alternatively, the attachment device 510 may comprise a hydrocolloid adhesive, which can substantially reduce or prevent skin irritation.

As illustrated in the example of FIG. 5, some embodiments of the manifold 405 may have flexibility notches 540. The flexibility notches 540 may be parallel to the line of symmetry 445, perpendicular to the line of symmetry 445, or both. Additionally or alternatively, one or more of the flexibility notches 540 may be oblique to the line of symmetry 445. In some embodiments, only the stem 410 may have the flexibility notches 540. In other embodiments, only the first arm 415, the second arm 420, or both may have the flexibility notches 540.

The thickness of the manifold 405 may vary according to prescribed therapy. In some embodiments, the manifold 405 or some portion of the manifold 405 may comprise felted, open-cell foam to increase rigidity. Additionally or alternatively, the manifold 405 may comprise foam segments having different density. For example, the stem 410 may comprise or consist essentially of open-cell foam having a higher density than the first arm 415 and the second arm 420.

The cover 140 may be larger than the manifold 405, as illustrated in the example of FIG. 5, and may have a perimeter configured to be attached to the attachment device 510. For example, the cover 140 may have a flange 545. Assembled, the cover 140 may be disposed over the face 425, and the flange 545 may be attached to the attachment device 510 around the manifold 405. For example, an adhesive may be used to adhere the flange 545 to the attachment device 510, or the flange 545 may be welded, stitched, or stapled to the attachment device 510. The cover 140 also has an aperture 550 and an expansion zone 555 in the example of FIG. 5. The aperture 550 can allow fluid communication between the manifold 405 and a dressing interface or fluid conductor. The expansion zone 555 may comprise folds, ribs, bellows, or other means for allowing the cover 140 to expand if needed.

Some embodiments of the dressing 110 may additionally include a comfort layer (not shown) coupled to the manifold and at least partially exposed through the treatment area aperture 515. The comfort layer may comprise or consist essentially of a material that substantially reduces or eliminates skin irritation while allowing fluid transfer through the comfort layer. Examples of materials that may be suitable include woven or non-woven textiles and fenestrated polymer films.

The center release liner 520, the first side release liner 525, and the second side release liner 530 may cover any adhesive on the attachment device 510. Additionally or alternatively, the center release liner 520, the first side release liner 525, and the second side release liner 530 may provide stiffness to the attachment device 510 to facilitate handling and application. Additionally or alternatively, the casting sheet liners 535 may cover the flange 545 to provide stiffness to the cover 140 for handling and application.

Figure 6:
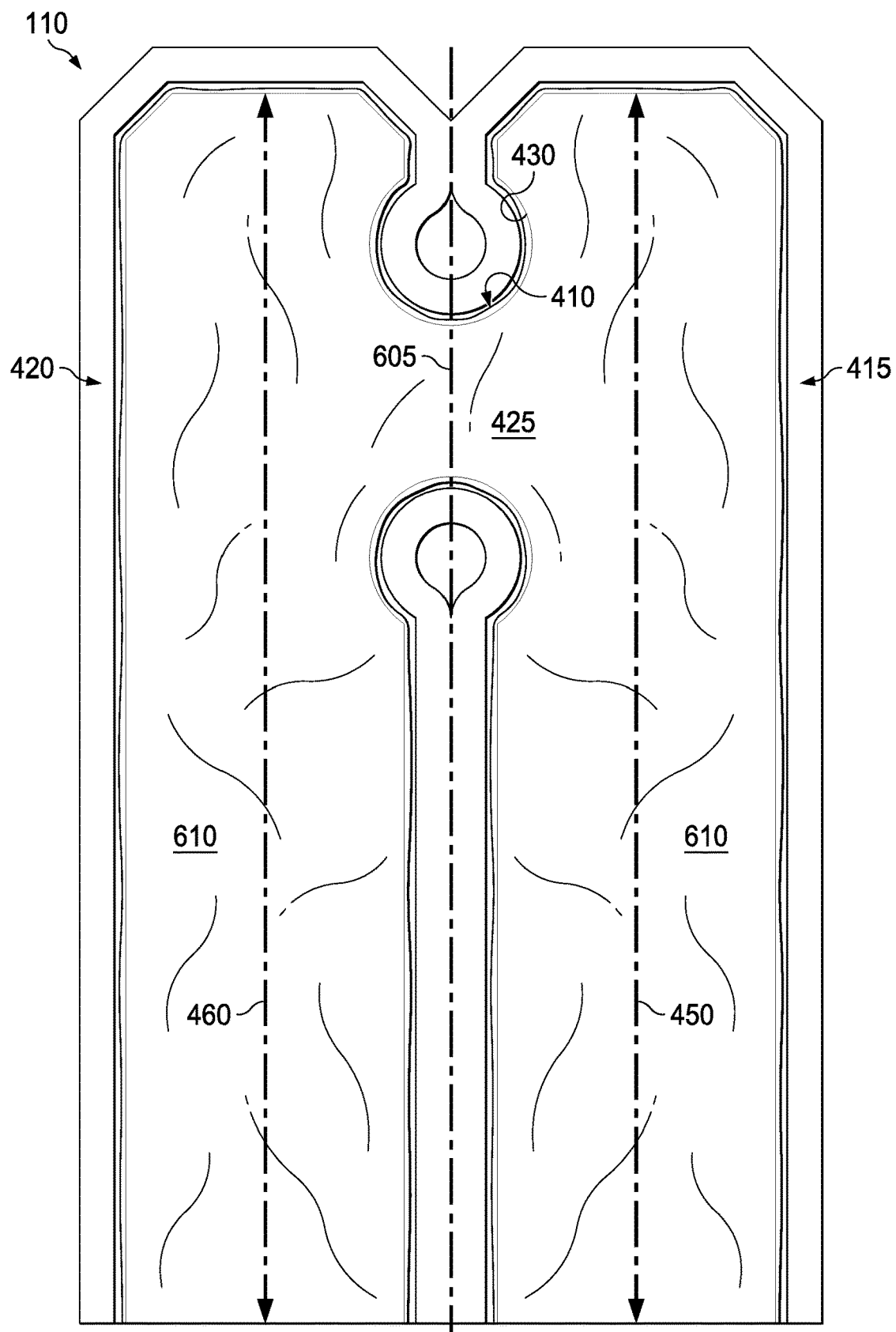
FIG. 6 is a top view of another example of the dressing, illustrating additional details that may be associated with some embodiments.

FIG. 6 is a top view of another example of the dressing 110, illustrating additional details that may be associated with some embodiments. The dressing 110 of FIG. 6 is similar the dressing 110 of FIG. 4 in many respects. For example, the face 425 of the dressing 110 of FIG. 6 may be biconcave. More generally, portions of the edge 430 bounding the first arm 415 and the second arm 420 may converge toward the stem 410 to define a concave void adjacent to each side of the stem 410.

The manifold 405 may additionally be characterized by a line of symmetry 605 through the stem 410, and each of the first arm 415 and the second arm 420 may be characterized by a span that is generally parallel to the line of symmetry 605. In the example of FIG. 6, the first span 450 and the second span 460 are substantially equal. The stem 410 in the example of FIG. 6 is offset from a center of the first span 450 and the second span 460. Thus, the first arm 415 and the second arm 420 each have a sacrificial extension portion 610 on one side of the stem 410.

In some embodiments, the manifold 405 may have distinct pressure zones. For example, the stem 410 may be fluidly isolated from the first arm 415, the second arm 420, or both. Each pressure zone may have a distinct fluid interface in some embodiments.

The cover 140, the manifold 405, the attachment device 510, or various combinations may be assembled before application or in situ. In some embodiments, the dressing 110 may be provided as a single unit.

In use, the center release liner 520 may be removed from the dressing 110, exposing a portion of the attachment device 510. The manifold 405 may be placed within, over, on, or otherwise proximate to a tissue site, and the exposed portion of the attachment device 510 may be placed against epidermis adjacent to the tissue site. If the tissue site is an incision, for example, the manifold 405 may be placed over the incision. In some embodiments, the line of symmetry 445 may be aligned with some or all of the incision. If the tissue site is on a limb, the first arm 415 may be wrapped around a proximal portion of the limb and the second arm 420 may be wrapped around a distal portion of the limb. The first arm 415 and the second arm 420 may not directly contact the incision in some applications, and a stronger adhesive may be used to secure at least portions of the first arm 415 and the second arm 420 to epidermis adjacent to the incision. The first side release liner 525 and the second side release liner 530 may be removed and applied to additional epidermis adjacent to the tissue site. Thus, the dressing 110 can provide a sealed therapeutic environment proximate to a tissue site, substantially isolated from the external environment, and the negative-pressure source 105 can be fluidly coupled to the manifold 405 through the aperture 550.

Figure 7:
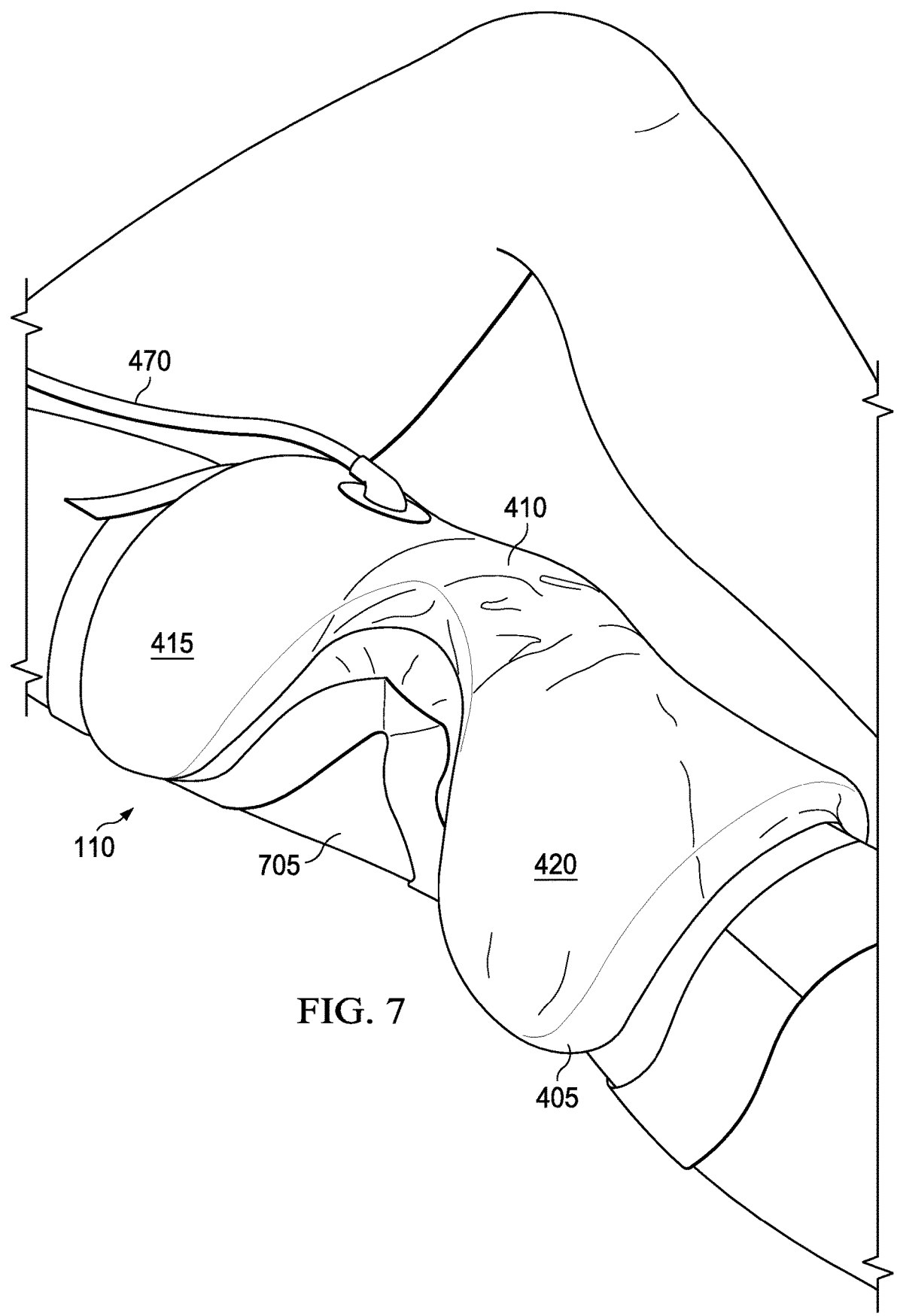
FIG. 7 illustrates the dressing of FIG. 4 applied to an articulating joint.

FIG. 7 illustrates the dressing 110 of FIG. 4 applied to an incision (not shown) on an articulating joint. In the example of FIG. 7, the articulating joint is a knee 705. As illustrated in the example of FIG. 7, the stem 410 may substantially cover the top of the knee 705. The manifold 405 is preferably oriented so that the first arm 415 and the fluid conductor 470 are superior to the knee 705. The first arm 415 may cover and wrap around a portion of the leg superior to the knee 705, and the second arm 420 may cover and wrap around a portion of the leg inferior to the knee 705. In some embodiments, one or more of the first arm 415 and the second arm 420 may be cut to reduce the first span 450, the second span 460, or both. For example, in the dressing 110 of FIG. 6, the extension portion 610 of the first arm 415, the second arm 420, or both may be cut so that the first arm 415 and the second arm 420 can fully wrap a portion of the leg superior and inferior to the knee 705, respectively.

Figure 8:
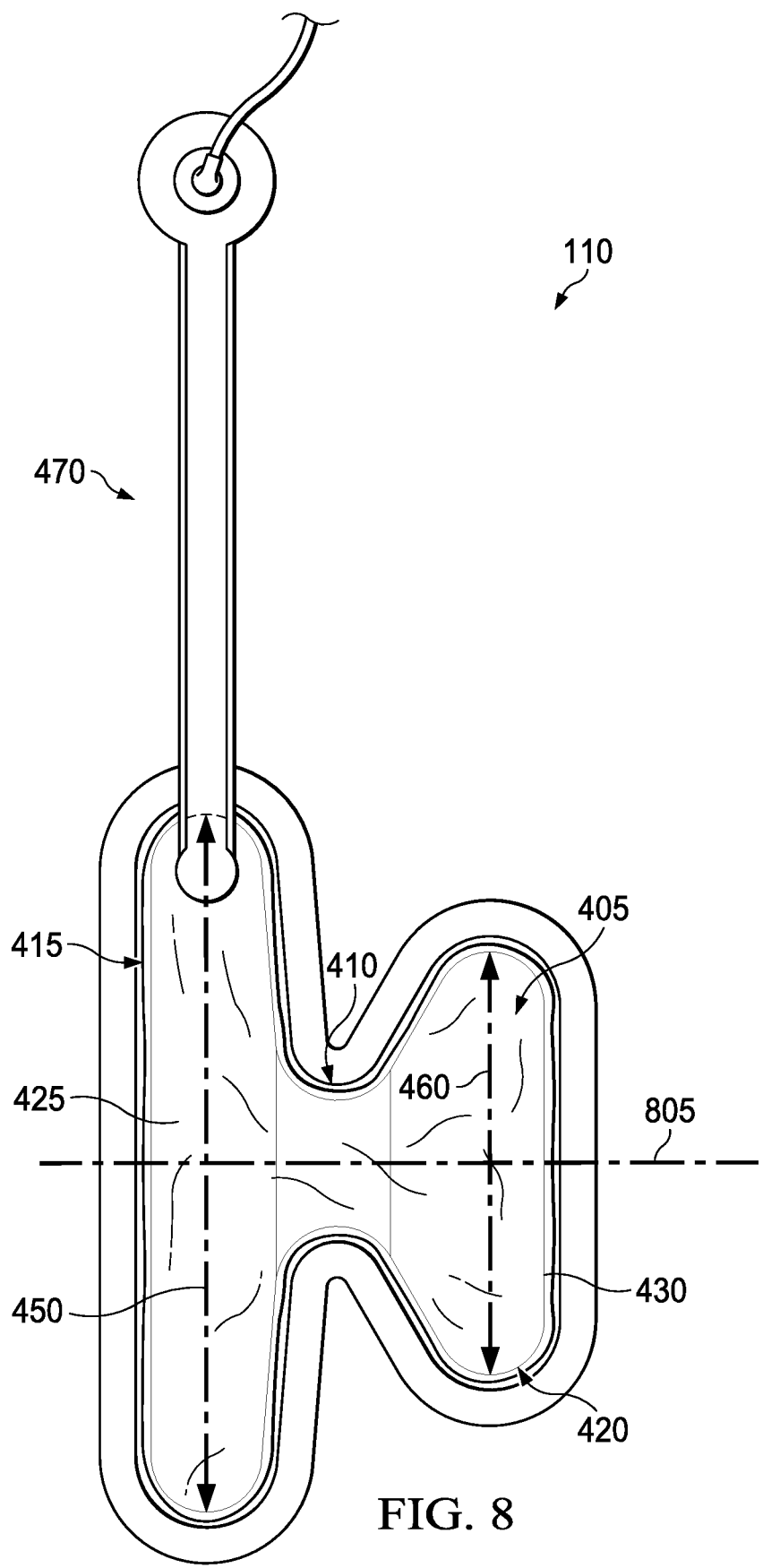
FIG. 8 is a top view of another example of a dressing, illustrating additional details that may be associated with some embodiments.

FIG. 8 is a top view of another example of the dressing 110, illustrating additional details that may be associated with some embodiments. In the example embodiment of FIG. 8, the dressing 110 includes features that can be applied to an ankle and surrounding tissue. The dressing 110 of FIG. 8 is similar the dressing 110 of FIG. 4 in many respects, and may have a similar construction. For example, the first arm 415 and the second arm 420 may flare away from the stem 410. In some examples, the face 425 may be biconcave. More generally, portions of the edge 430 bounding the first arm 415 and the second arm 420 may converge toward the stem 410 to define a concave void adjacent to each side of the stem 410. In the example of FIG. 8, the concave void is curved. In other examples, the edge 430 may have straight segments that converge toward a vertex at the stem 410. More generally, portions of the edge 430 bounding the first arm 415 and the second arm 420 may converge toward the stem 410 to define a concave void adjacent to each side of the stem 410.

The manifold 405 of FIG. 8 may additionally be characterized by a line of symmetry 805 through the stem 410, and each of the first arm 415 and the second arm 420 may be characterized by a span that is generally orthogonal to the line of symmetry 805. In the example of FIG. 8, the first span 450 is greater than the second span 460. For example, in some embodiments the first span 450 may be in a range of 15-25 centimeters and the second span 460 may be in a range of 10-15 centimeters. As illustrated in FIG. 8, the first arm 415 may be coupled to the fluid conductor 470, which may be a low-profile dressing bridge.

Figure 9:
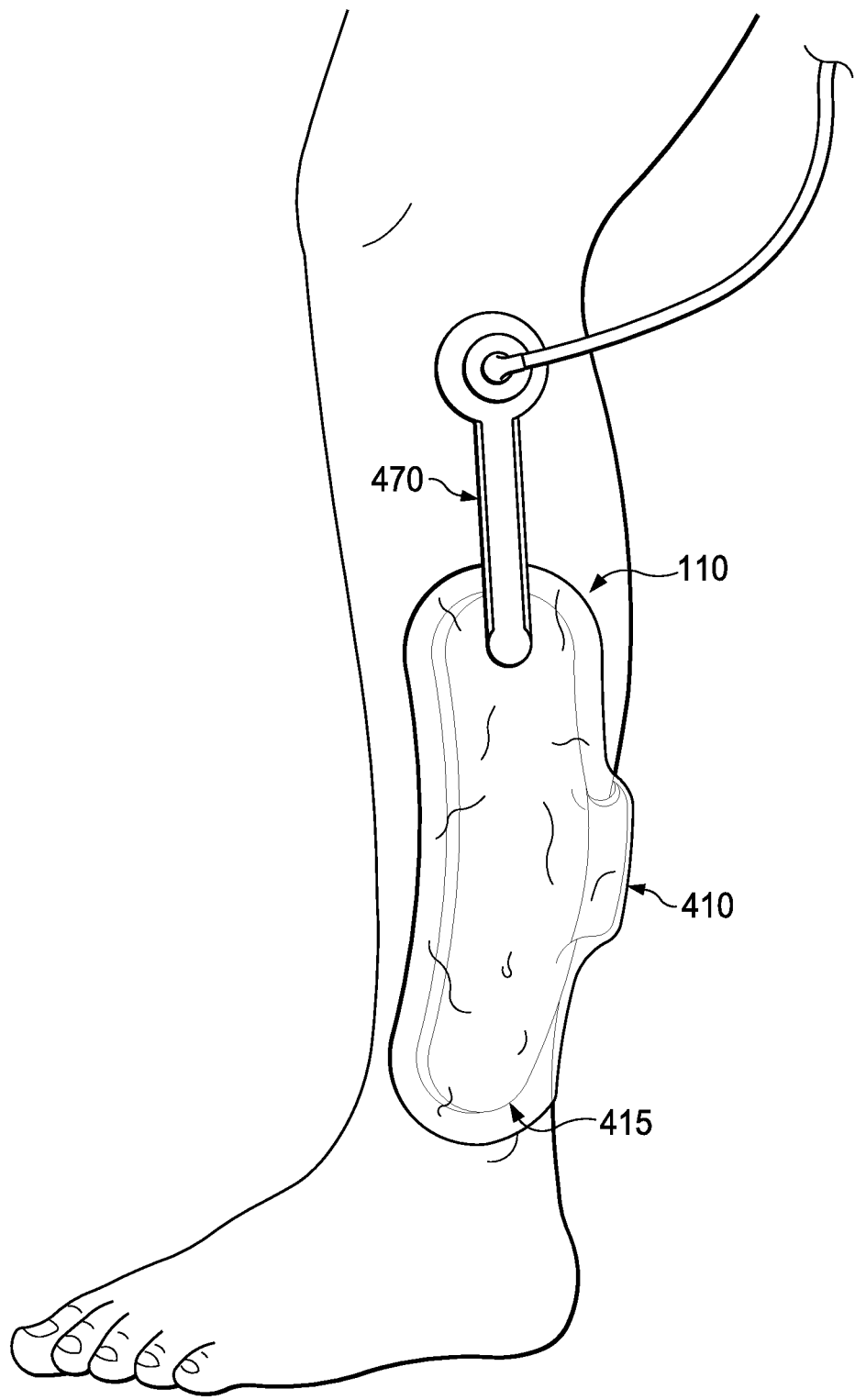
FIG. 9 illustrates the dressing of FIG. 8 applied to an incision on an ankle and adjacent tissue.

FIG. 9 illustrates the dressing 110 of FIG. 8 applied to an incision (not visible) on an ankle and adjacent tissue. The stem 410 may be placed superior to the foot, on either the anterior or posterior side of a leg. The first arm 415 may be disposed over a lateral portion of the leg or over a medial portion of the leg, depending on placement of the stem 410. The second arm 420 may also be disposed over a lateral portion or a medial portion depending on placement of the stem 410. For example, if the incision is shorter than the length of the second arm 420, the dressing 110 may be oriented so that either the first arm 415 or the second arm 420 is disposed over the incision. On other examples, if the incision is longer than the length of the second arm 420, the dressing 110 may be oriented so that the first arm 415 covers the incision.

In some examples, the dressing 110 may be oriented to cover more than one incision. Additionally or alternatively, a support boot (not shown) may be worn over the dressing 110 in some examples. The fluid conductor 470 of FIG. 9 can also be partially disposed beneath the boot, and can be partially extending above a top of the boot to provide a convenient access point for coupling the dressing 110 to the negative-pressure source 105 or another distribution component.

Figure 10:
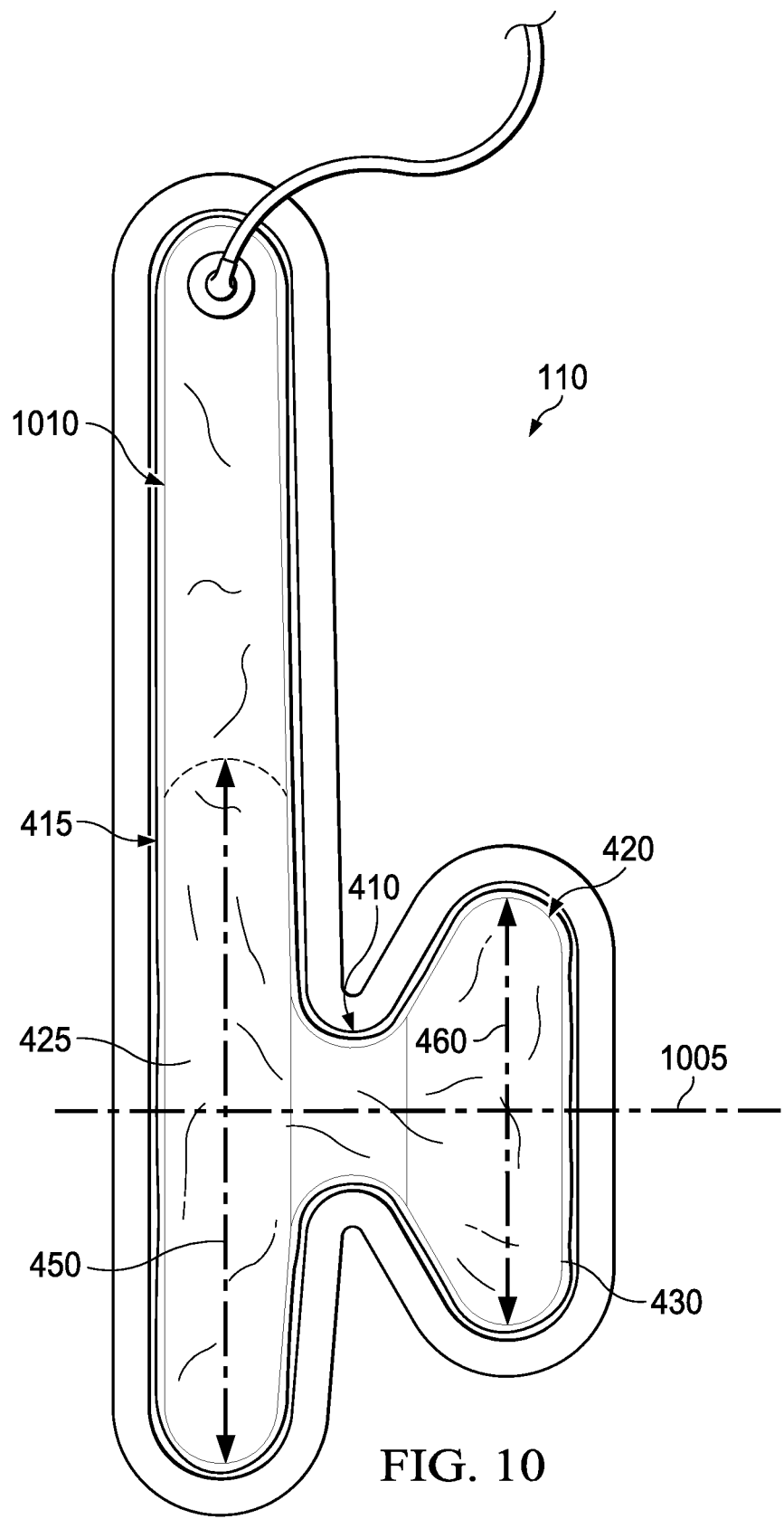
FIG. 10 is a top view of another example of a dressing, illustrating additional details that may be associated with some embodiments.

FIG. 10 is a top view of another example of the dressing 110, illustrating additional details that may be associated with some embodiments. In the example embodiment of FIG. 10, the dressing 110 includes features that can cover an ankle and surrounding tissue. The dressing 110 of FIG. 8 is similar the dressing 110 of FIG. 8 in many respects. For example, the first arm 415 and the second arm 420 may flare away from the stem 410. In some examples, the face 425 may be biconcave. More generally, portions of the edge 430 bounding the first arm 415 and the second arm 420 may converge toward the stem 410 to define a concave void adjacent to each side of the stem 410. In the example of FIG. 10, the concave void is curved. In other examples, the edge 430 may have straight segments that converge toward a vertex at the stem 410. More generally, portions of the edge 430 bounding the first arm 415 and the second arm 420 may converge toward the stem 410 to define a concave void adjacent to each side of the stem 410.

The manifold 405 of FIG. 10 may additionally be characterized by a line of symmetry 1005 through the stem 410, and each of the first arm 415 and the second arm 420 may be characterized by a span that is generally orthogonal to the line of symmetry 1005. In the example of FIG. 8, the first span 450 is greater than the second span 460. For example, in some embodiments the first span 450 may be in a range of 15-25 centimeters and the second span 460 may be in a range of 10-15 centimeters. As illustrated in FIG. 10, the first arm 415 may have or may be coupled to an arm extension 1010. The fluid conductor 470 may be coupled to the arm extension 1010.

Figure 11:
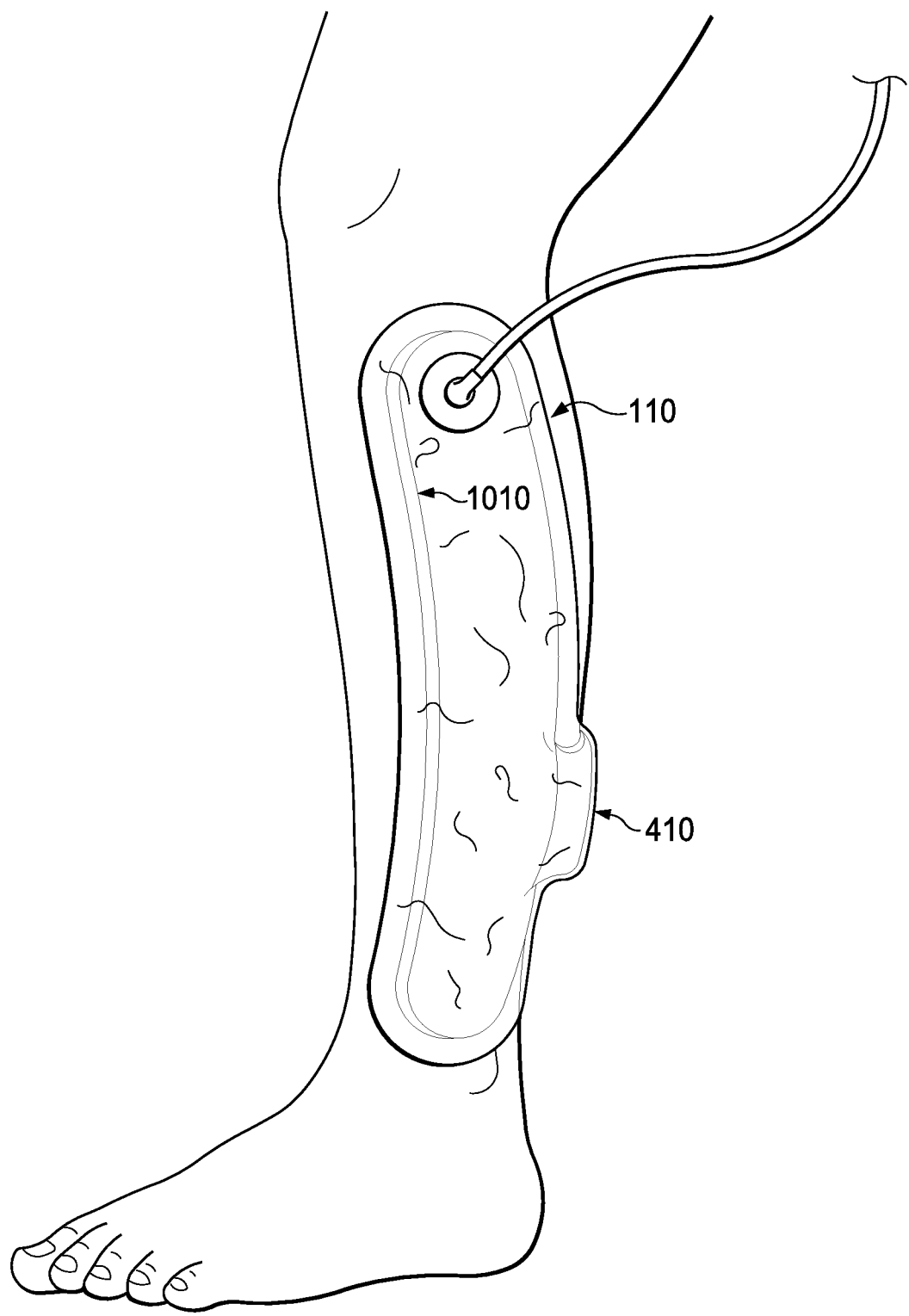
FIG. 11 illustrates the dressing of FIG. 10 applied to an incision on an ankle and adjacent tissue.

FIG. 11 illustrates the dressing 110 of FIG. 10 applied to an incision (not visible) on an ankle and adjacent tissue. The stem 410 may be placed superior to the foot, on either the anterior or posterior side of a leg. The first arm 415 may be disposed over a lateral portion of the leg or over a medial portion of the leg, depending on placement of the stem 410. The second arm 420 may also be disposed over a lateral portion or a medial portion depending on placement of the stem 410. For example, if the incision is shorter than the length of the second arm 420, the dressing 110 may be oriented so that either the first arm 415 or the second arm 420 is disposed over the incision. On other examples, if the incision is longer than the length of the second arm 420, the dressing 110 may be oriented so that the first arm 415 covers the incision.

In some examples, the dressing 110 may be oriented to cover more than one incision. Additionally or alternatively, a support boot (not shown) may be worn over the dressing 110 in some examples. The arm extension 1010 of FIG. 11 can also be partially disposed beneath a boot, and can be partially extending above a top of the boot to provide a convenient access point for coupling the dressing 110 to the negative-pressure source 105 or another distribution component.

In operation, the negative-pressure source 105 can reduce pressure in the sealed therapeutic environment. Negative pressure applied across the tissue site through the manifold 405 in the sealed therapeutic environment can induce macro-strain and micro-strain in the tissue site, as well as remove exudates and other fluids from the tissue site, which can be collected in the container 115.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

In some embodiments, the controller 120 may receive and process data from one or more sensors, such as the first sensor 125. The controller 120 may also control the operation of one or more components of the therapy system 100 to manage the pressure delivered to the tissue interface 135. In some embodiments, controller 120 may include an input for receiving a desired target pressure, and may be programmed for processing data relating to the setting and inputting of the target pressure to be applied to the tissue interface 135. In some example embodiments, the target pressure may be a fixed pressure value set by an operator as the target negative pressure desired for therapy at a tissue site and then provided as input to the controller 120. The target pressure may vary from tissue site to tissue site based on the type of tissue forming a tissue site, the type of injury or wound (if any), the medical condition of the patient, and the preference of the attending physician. After selecting a desired target pressure, the controller 120 can operate the negative-pressure source 105 in one or more control modes based on the target pressure, and may receive feedback from one or more sensors to maintain the target pressure at the tissue interface 135. In some embodiments, the manifold 405 may have distinct pressure zones, and different target pressures and control modes may be applied to different pressure zones.

The systems, apparatuses, and methods described herein may provide significant advantages. For example, in addition to benefits of increase development of granulation tissue and reduce healing times of incisions, the therapy system 100 can also reduce edema and bruising in a broader area adjacent to an incision. The dressing 110 can reduce stress on an incision and maximize coverage area of articulating joints, while still allowing for range of motion. The dressing 110 can also be beneficial for managing edema and bruising of tissue sites without an incision or open wound, such as a sprain. In some embodiments, the features of the dressing 110 may allow an area to be treated for up to 14 days without changing the dressing 110.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 110, the container 115, or both may be eliminated or separated from other components for manufacture or sale. In other example configurations, the controller 120 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A dressing for treating an area around an ankle with negative pressure, the dressing comprising:
    a foam manifold comprising a stem, a first arm joined to the stem, and a second arm joined to the stem, the first arm comprising an arm extension for coupling to a fluid conductor, wherein the stem comprises foam having a higher density than the first arm and the second arm;

an attachment device including a first surface and a second surface, the first surface coupled to a periphery of a tissue-facing side of the manifold, the attachment device comprising a treatment aperture configured to at least partially expose the manifold;

a cover disposed over the manifold and coupled to the attachment device around the manifold; and an adhesive on the second surface of the attachment device configured to bond to the area around the ankle.

2. The dressing of claim 1, wherein the first arm has a greater span than the second arm.

3. The dressing of claim 1, wherein:
the first arm has a first span;
the second arm has a second span; and
a ratio of the first span to the second span is about 1.5.

4. The dressing of claim 1, wherein the first arm and the second arm flare away from the stem.

5. The dressing of claim 1, wherein the first arm and the second arm comprise converging edges.

6. The dressing of claim 1, wherein the stem, the first arm, and the second arm define biconcave edges.

7. The dressing of claim 1, wherein the manifold comprises a face that is biconcave.

8. The dressing of claim 1, wherein the manifold has a line of symmetry through the stem.

9. The dressing of claim 1, wherein:
the manifold has a line of symmetry through the stem; and
the first arm and the second arm define a void adjacent to each side of the stem.

10. The dressing of claim 1, wherein:
the manifold has an edge bounding the first arm and the second arm; and
a portion of the edge bounding the first arm and the second arm converges toward the stem to define a concave void adjacent to each side of the stem.

11. The dressing of claim 1, further comprising a dressing interface fluidly coupled to the first arm through the cover.

12. The dressing of claim 1, further comprising a comfort layer coupled to the manifold, the comfort layer at least partially exposed through the treatment aperture.

13. The dressing of claim 1, wherein the adhesive is disposed in a border of the attachment device.

14. The dressing of claim 1, wherein the attachment device further comprises a sealing ring around the treatment aperture.

15. The dressing of claim 14, wherein the sealing ring comprises a hydrocolloid.

16. The dressing of claim 1, wherein:
the stem is configured to be placed over a portion of a leg above the ankle;
the first arm is configured to be placed over a lateral portion of the leg; and
the second arm is configured to be placed over a medial portion of the leg.

17. The dressing of claim 1, wherein:
the manifold has a line of symmetry through the stem;
the first arm is asymmetrical about the line of symmetry; and
the second arm is symmetrical about the line of symmetry.

18. The dressing of claim 1, wherein the arm extension is coupled to the first arm.

19. The dressing of claim 1, further comprising a dressing bridge configured to fluidly couple the fluid conductor to the first arm.

20. The dressing of claim 1, further comprising:
a first side release liner configured to be releasably coupled to the attachment device on a first side of the manifold;
a second side release liner configured to be releasably coupled to the attachment device on a second side of the manifold opposite the first side; and
a center release liner configured to be releasably coupled to the attachment device at a center portion of the manifold.

* * * * *